United States Patent [19]

Siegl

[11] 4,115,397
[45] Sep. 19, 1978

[54] METAL CHELATING LIGANDS
[75] Inventor: Walter O. Siegl, Dearborn, Mich.
[73] Assignee: Ford Motor Company, Dearborn, Mich.
[21] Appl. No.: 805,054
[22] Filed: Jun. 9, 1977

Related U.S. Application Data

[63] Continuation-in-part of Ser. No. 793,587, May 4, 1977.
[51] Int. Cl.² .................................. C07D 487/04
[52] U.S. Cl. .................. 260/296 T; 44/63; 260/42.21
[58] Field of Search .......... 260/297 T, 313.1, 319.1, 260/326.15

[56] References Cited

PUBLICATIONS

Siegl, Abstract of Metal Complexes of bis–1,3–(-2–pyridyl)iminoisoindoline and Related Ligands.
Siegl, Preliminary Communication, Journal of Organometallic Chemistry, vol. 107, pp. C27–C30, (1976).
Packham et al, Polymer, vol. 10, pp. 563 and 571, (1969).
Manecke et al., Makromol. Chem., vol. 120, pp. 192 to 209, (1969).

*Primary Examiner*—John D. Randolph
*Attorney, Agent, or Firm*—Edmund C. Ross, Jr.; Olin B. Johnson

[57] ABSTRACT

Alkyl substitution at the pyridyl periphery of 1, 3, 5, 7-tetra (2-pyridylimino)-benzodipyrroles provides bis chelating ligands with unexpected increase in organic solubility. The bis-chelating ligands may be used to form organometallic polymers as well as being suitable as dyes and metal ion deactivators. The metal complexes of such bis-chelating ligands may also be used as dyes.

3 Claims, No Drawings

METAL CHELATING LIGANDS

This application is a continuation-in-part of U.S. application Ser. No. 793,587, filed May 4, 1977, entitled "Organometallic Polymers (A)".

THE INVENTION

This invention concerns bis-chelating ligands having unexpected increases in organic solubility. The bis-chelating ligands are represented as:

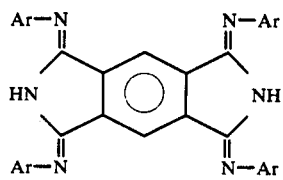

wherein each Ar is:

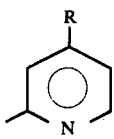

and each R is independently hydrogen or straight or branched chain alkyl of up to about 20 carbon atoms, providing that (a) the sum of the carbon atoms in all R's is at least 8 and (b) no more than one R has a tertiary-alpha carbon atoms connected to the heterocycle. Preferably, each R is at least two carbons, and, preferably, attached to the remainder of the molecule such that the carbon atoms of R alpha to the heterocycle is secondary, e.g., R is sec-butyl or isopropyl.

Each end of the planar bis-chelating ligand functions independently as a univalent, tridentate ligand which may occupy three co-planar sites of a square planar, trigonal bipyramidal, or octahedral coordination sphere. Further, the tridentate nature of each end of the bis-chelating ligand permits preparation of organometallic polymers, the subject of my copending application Ser. No. 793,587, filed on May 4, 1977. The organic solubility attained by inclusion of alkyl substitution R at the pyridyl perifery facilitates preparation and use of such organometallic polymers in organic media.

The bis-chelating ligands of this invention can be obtained in two ways. In a first preparative route tetracyanobenzene is reacted with 2-amino-4-alkylpyridine in the presence of alkaline earth metal salt (e.g., calcium chloride) and lower alkanol (e.g., butanol). In a second preparative route, the aminopyridine is reacted in the presence of a divalent transition metal salt (e.g. nickel acetate) and lower alkanol (e.g. methanol) followed by removal of the metal acetate from the ligand by treatment with alkali metal cyanide (e.g., potassium cyanide).

This bis-chelating ligands are high melting, yellow crystalline solids. They form mono- and bimetal complexes and are especially suitable for chelating of first, second and third row divalent transition metal cations in organic media. Examples of metals chelated by the bis-chelating ligands herein are cobalt, nickel, copper, zinc, iridium, palladium and rhodium.

Since the chelation is with each of the tridentate, univalent ends, a chelated divalent metal cation is seen normally associated with an anion and such anion may be organic (e.g. acetate) or inorganic (e.g. chloride). There does not appear to be any limitation to the character of the anion as long as the salt thereof exhibits sufficient solubility in the chelating media.

The anion may be removed from the metal complex of the bis-chelating ligand by reaction with monochelating ligands such as 1,3-bis (2-pyridylimino) isoindoline thereby encapsulating the metal cation.

The following examples are intended as illustrating this invention and not intended as limiting thereof. All parts are parts by weight and all temperatures are in degrees centigrade.

PREPARATION OF AMINES

The amines which are used in preparation of the bis-chelating ligands of these examples may be prepared as illustrated below:

2-Amino-4-ethylpyridine. This amine is prepared by the method of Case and Kasper from 4-ethylpyridine (Aldrich Chemical) and sodium amide (Fisher Scientific Co.) in 55% molar yield, mp 66°–70° (lit.[1] 70°–1°).

2-Amino-4-propylpyridine. This amine is prepared using the general method of Case and Kasper[1] from 4-propyl-pyridine (Eastman) in 50% molar yield as deliquescent white crystals and was stored in a desiccator over Drierite.[2]

2-Amino-4-butylpyridine. This amine is prepared by the procedure of Case and Kasper[1] from 4-t-butylpyridine (Aldrich Chemical Co.) and is obtained as white needles, mp 82°–3° in 12% molar yield.

2-Amino-4-amylpyridine. This amine is prepared by the method of Case and Kasper[1] from 4-n-amylpyridine (K and K Laboratories) and is obtained as colorless crystals, mp 55°–6° (lit.[3] 58°–58.5° )in 58% molar yield.

4-sec-butylpyridine. A method similar to that of Brown and Murphey is employed.[4] Approximately 500 ml of $NH_3$ was condensed in a 1-liter flask; 1 mole of sodium amine (Fisher) followed by 1.0 mole of 4-ethylpyridine is added to the flask. After stirring under $NH_3$ reflux for 30 minutes, 1.1 mole of ethyl iodide is added via an addition funnel to the orange-red suspension over a 1.5 hour period. Stirring is continued after the ethyliodide addition is complete and the solvent is allowed to evaporate slowly. Water (50 ml) is added to the residue and the layers are separated. The aqueous layer is extracted with ether and the combined organic layers are dried over $Na_2CO_3$, concentrated, and distilled. A colorless oil, 117.2 gm (87%), bp 120–25/90mm (lit.[5] 128°–30°/100 mm) is collected. The oil exhibits an nmr signal typical for a sec-butyl group in addition to the usual pattern for 4-substituted pyridine.

2-Amino-4-sec-butylpyridine. This 2-aminopyridine is prepared according to the general procedure of Case and Kasper[1] from 4-sec-Butylpyridine (described above). The product was obtained as white crystals (49%), mp 64°–5°, nmr (CDCl$_3$): δ 7.9(d) 1H, 6.44(d) 1H, 6.29(s) 1H, 4.66 (s. br) 2H, 2.48(m) 1H, 1.57(m) 2H, 1.19(d) 3H, 0.94(t) 3H.

Anal. Calcd for $C_9H_{14}N_2$: C, 71.95; H, 9.39; N, 18.65. Found: C, 71.97; H, 9.32; N, 18.70.

1. F. H. Case and T. J. Kasper, *J. Amer. Chem. Soc.*, 78, 5842 (1956).
2. W. Solomon, *J. Chem. Soc.* 934 (1946).
3. F. H. Case and W. A. Butte, *J. Org. Chem.*, 26,4415 (1961).
4. H. C. Brown and W. A. Murphey, *J. Amer. Chem. Soc.*, 73, 3308 (1951).
5. W. M. Stalick and H. Pines, *J. Org. Chem.*, 35, 422 (1970).

PREPARATION OF BIS-CHELATING LIGANDS

EXAMPLE I

A round bottom flask is charged with 1 part 1,2,4,5-tetracyanobenzene, 3.96 parts 2-aminopyridine, 0.626 parts calcium chloride and 56 parts ethyl alcohol. The mixture is stirred for 10 days at 25° C.; then 67 parts 2-methoxyethanol is added and the ethanol is distilled off from the reaction mixture. The remaining yellow suspension is heated at reflux for 8 days. After cooling, the product is filtered and the residue washed with water/methanol and again with acetone. After drying, a greenish yellow powder is obtained which is crystallized from hot quinoline (MP 397°–9° C.). The greenish yellow powder contains the desired 1,3,5,7-tetra (2-pyridylimino)-benzodipyrrole. The 1,3,5,7-tetra (2-pyridylimino)-benzodipyrrole has a solubility in benzene at 23° C. of $1.64 \times 10^{-4}$ moles per liter.

EXAMPLE II

Following the general procedure of Example I, the bis-chelate ligands IIa–IIf are prepared from 1,2,4,5-tetracyanobenzene and the heterocyclic primary amines as follows:

| Compound | Primary Amine N-Heterocycle | Mp[1] | RS[2] |
| --- | --- | --- | --- |
| II a | 2-amino - 4-methylpyridine | 340–1 ° C | 0.4 |
| II b | 2-amino - 4-ethylpyridine | 353–5 ° C | 28 |
| II c | 2-amino - 4-propylpyridine | 357–9 ° C | 20 |
| II d | 2-amino - 4-t-butylpyridine | 435–7 ° C | 0.7 |
| II e | 2-amino - 4-s-butylpyridine | 369–71 ° C | 41 |
| II f | 2-amino - 4-n-amylpyridine | 317–8 ° C | 4.5 |

[1]Melting point of resultant bis-chelate ligand.
[2]Relative solubility in benzene at 23° C as compared to the bis-chelating ligand of Example I.

All ligands tested give confirmatory ir, nmr, and elemental analysis.

EXAMPLE III

A flask is charged with 1 part bis-chelating ligand IIe, 3.4 parts nickel acetate, and 27 parts methanol. The mixture is stirred for two days at 24° C., then filtered. The residue is washed with water and methanol and then dried. The nickel acetate complex of IIe is obtained as a rust color powder.

EXAMPLE IV

A flask is charged with 1 part 1,2,4,5-tetracyanobenzene, 3.7 parts 2-amino-4-sec-butylpyridine, 2.8 parts nickel acetate, and 89 parts methanol. The mixture is stirred for 30 hours at 24° C., then for 5 days at reflux. The solvent is evaporated from the reaction mixture and the residue is washed with methanol and with water. After drying, the nickel acetate complex of IIe is obtained as a rust color powder which is spectroscopically identical to that obtained in Example III.

EXAMPLE V

The procedure of Example IV is followed except cupric acetate (2.25 parts) is used rather than nickel acetate. The cupric acetate complex of bis-chelating ligand IIe is obtained as a green powder.

EXAMPLE VI

A flask is charged with 1 part of the nickel acetate complex of IIe (described in Example III), 1.5 parts potassium cyanide, and 32 parts ethanol. The mixture is stirred at reflux for 8 hours, then 60 parts chloroform is added and the mixture is stirred for 48 hours at 24° C. The solvent is distilled off and the residue is washed with water. The dried residue is recrystallized from benzene to give bis-chelating ligand IIe.

EXAMPLE VII

A flask is charged with 2.11 parts of bis-chelating ligand IIe, 2.17 parts dichlorobis (benzonitrile)-palladium (II), 1 part sodium carbonate, and 1900 parts acetone. The suspension is stirred for 6 hrs. at 24° C. under argon and then filtered in the air. The residue is washed with water and with acetone. After drying 2.63 parts of orange powder, corresponding to the palladium chloride complex with IIe, is obtained. The powder analyzed for: %C; 53.94; H, 5.03; N, 13.75; calculated for $C_{46} H_{50} N_{10} Pd_2 Cl_2$: C, 53.83; H, 4.91; N, 13.64.

EXAMPLE VIII

A flask is charged with 1 part bis-chelating ligand IIe, 1.34 parts cupric acetate hydrate and 85 parts ethanol. The mixture is stirred at 24° for 3 days after which the solvent is evaporated at reduced pressure. The residue is washed with water and then dried to yield 95% of the copper acetate complex of IIe as a gold powder. Recrystallization of the powder from methylene chloride - hexane afforded the product as green-gold needles. The crystals analyzed for: C, 60.21; H, 5.67; N, 14.11; calculated for $C_{50} H_{56} N_{10} O_4 Cu_2$: C, 60.77; H, 5.71; N, 14.18.

These bis-chelating ligands, as well as metal complexes thereof, as hereinbefore mentioned, can be used as dyes. The bis-chelating ligand advantageously provides a yellow coloration or thermoplastics such as polyvinylchloride resins at levels of 1 part by weight bis-chelating ligand to up to 4000 parts by weight resin. Moreover, the bis-chelate ligand can be used at levels of 1 part ligand up to about 10,000 parts hydrocarbon (e.g. gasoline) as a metal ion deactivator for such metals as copper and zinc. Other organic media for which these bis-chelating ligands are suitable include polar organic media such as liquid aromatic and aliphatic halides, hydroxy, ether and like compounds as well as non-polar compounds such as hydrocarbons of aromatic or aliphatic character.

What is claimed is:

1. A bis-chelating ligand corresponding to the formula:

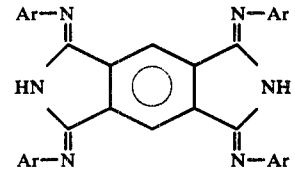

wherein each Ar is:

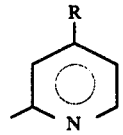

and each R is independently hydrogen or straight or branched chain alkyl of up to about 20 carbon atoms, providing that (a) the sum of the carbon atoms in all R's is at least 8 and (b) no more than one R has a tertiary carbon atom connected to the heterocycle.

2. The bis-chelating ligand in accordance with claim 1 wherein at least one R has an alpha carbon which is a secondary carbon atom.

3. The bis-chelating ligand of claim 2 wherein each R is sec-butyl.

* * * * *